United States Patent [19]

Vara et al.

[11] Patent Number: 4,902,310

[45] Date of Patent: Feb. 20, 1990

[54] PROCESS FOR REMOVING HALOGENATED HYDROCARBONS FROM SOLVENT STREAMS

[75] Inventors: Thomas E. Vara; Jerald L. Mestemaker, both of Vero Beach, Fla.

[73] Assignee: Vara International, Inc., Vero Beach, Fla.

[21] Appl. No.: 352,479

[22] Filed: May 16, 1989

Related U.S. Application Data

[63] Continuation-in-part of Ser. No. 286,655, Dec. 19, 1988.

[51] Int. Cl.$^4$ ............................................. B01D 5/00
[52] U.S. Cl. ........................................... 55/46; 55/48; 55/51; 55/59
[58] Field of Search ................... 55/46, 48, 51, 59, 62; 203/14, 39, 43, 71

[56] References Cited

U.S. PATENT DOCUMENTS

| | | |
|---|---|---|
| 2,760,594 | 8/1956 | Browning et al. . |
| 3,343,916 | 9/1967 | Cahn et al. ..................... 55/62 X |
| 3,883,325 | 5/1975 | Fuhring et al. . |
| 3,963,461 | 6/1976 | Stockford et al. . |
| 4,018,704 | 4/1977 | Kuragano . |
| 4,056,369 | 11/1977 | Quackenbush . |
| 4,219,537 | 8/1980 | Steiner . |
| 4,261,716 | 4/1981 | Schwartz et al. . |
| 4,276,058 | 6/1981 | Dinsmore ........................... 55/48 |
| 4,286,972 | 9/1981 | Savage et al. . |
| 4,289,505 | 9/1981 | Hardison et al. . |
| 4,331,456 | 5/1982 | Schwartz et al. . |
| 4,343,629 | 8/1982 | Dinsmore et al. . |
| 4,414,003 | 11/1983 | Blaudszun . |
| 4,487,614 | 12/1984 | Yon . |
| 4,553,983 | 11/1985 | Baker . |
| 4,661,256 | 4/1987 | Johnson . |
| 4,689,054 | 8/1987 | Vara et al. . |

FOREIGN PATENT DOCUMENTS 2703737 8/1978 Fed. Rep. of Germany .

OTHER PUBLICATIONS

Operations Improvements, by M. S. Thomas, Exec. V.P., Vara, Int'l, "Focus on Solvent Recovery".
"Spontaneous Combustion of Carbon Beds", by A. A. Navjokos, Eastman Kodak, Rochester, N.Y.
"Vapor-Phase Adsorption Cuts Pollution, Recovers Solvents" by C. S. Parmele; W. L. O'Connell, H. S. Basdekis of Hydroscience, Inc.
Special Report: Volatile Organic Compounds by Paul N. Cheremisinoff.
Solvent Recovery System Controls Pollution While Saving Money (flyer by Vara Int'l).
Solvent Recover-Answer to Efficient Pollution Control in Production of Pressure-Sensitive Materials (flyer by Vara, Int'l).

Primary Examiner—Charles Hart
Attorney, Agent, or Firm—Steele, Gould & Fried

[57] ABSTRACT

A process is provided for recovering halogenated hydrocarbons from solvent streams, particularly those including water and at least one alcohol, ketone or ester impurity. The process also provides for the recovery of the alcohol, ketone or ester, which can be reused or incinerated. The solvent stream is condensed and initially separated into a halogenated hydrocarbon rich fraction and a water rich fraction containing the impurities. Impurities are removed from the halogenated hydrocarbon rich fraction in a first separation step, preferably liquid-liquid extraction with water. The impurities are extracted from the halogenated hydrocarbons into the water, which is passed to the water fraction of the initial separation step for further treatment. Halogenated hydrocarbons leaving the extraction column are passed to a distillation column where remaining water and impurities are removed. A continuous halogenated hydrocarbon vapor draw is preferably removed and condensed from the distillation column. The halogenated hydrocarbon product from the distillation column can, if necessary, be further dehydrated prior to storage or reuse. The water rich fraction is processed in one or more separation steps to remove remaining halogenated hydrocarbons and impurities. The halogenated hydrocarbons are removed in a first water rich fraction distillation step, and the impurities are removed from the water in a second water rich fraction distillation step.

18 Claims, 1 Drawing Sheet

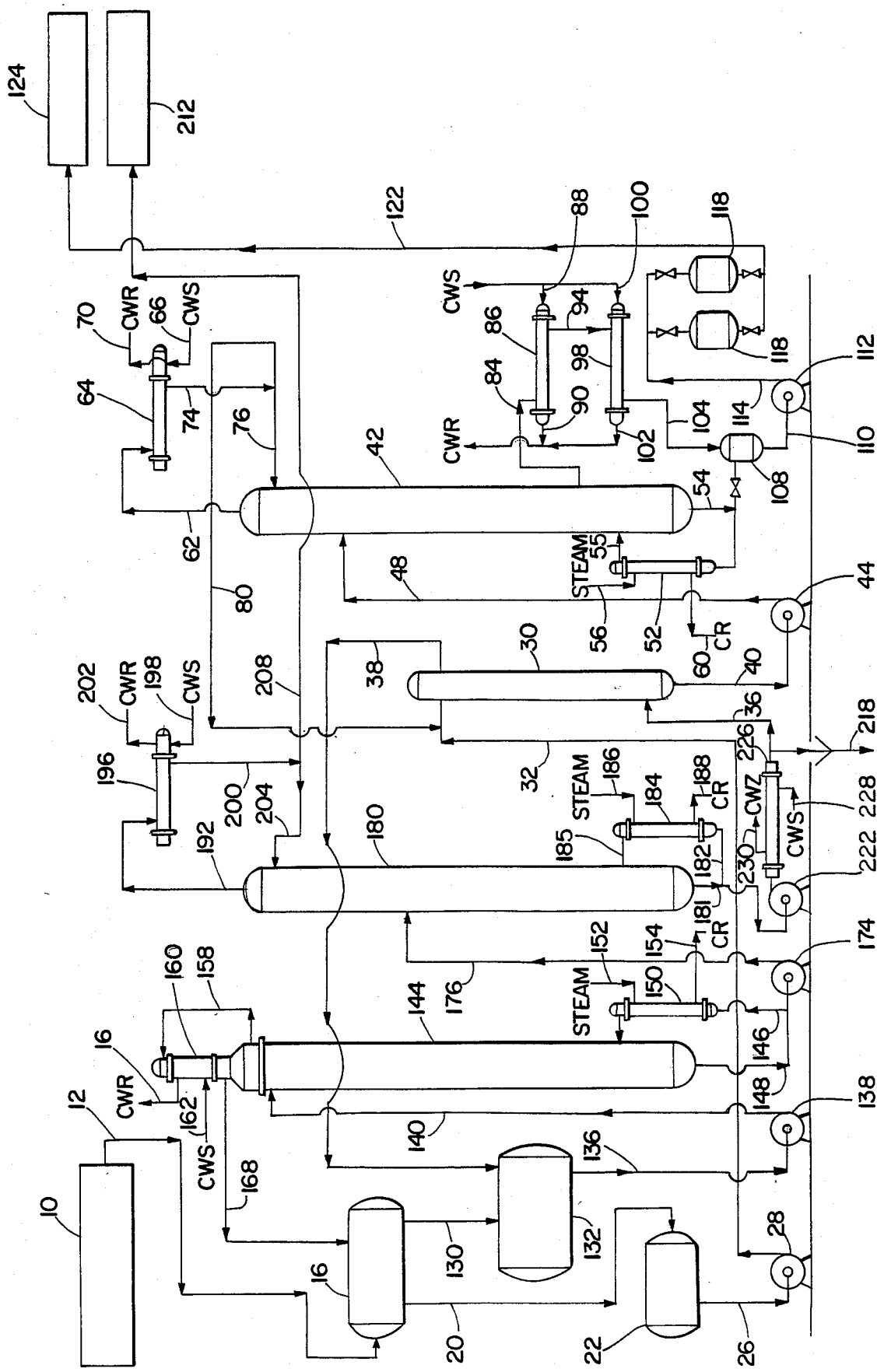

PROCESS FOR REMOVING HALOGENATED HYDROCARBONS FROM SOLVENT STREAMS

BACKGROUND OF THE INVENTION

CROSS REFERENCE TO RELATED APPLICATIONS

The present application is a Continuation-in-Part of Applicant's co-pending U.S. patent application Ser. No. 286,655, filed Dec. 19, 1988.

FIELD OF THE INVENTION

This invention relates generally to separation processes, and more particularly to processes for the recovery of halogenated hydrocarbons and impurities present in solvent streams.

DESCRIPTION OF PRIOR ART

Government regulatory agencies around the world have recognized a need to curtail the emission of halogenated hydrocarbons into the environment. It is therefore incumbent on manufacturers who utilize halogenated hydrocarbons to strictly control the emission of these materials, and to therefore remove these compounds from effluent process streams. Separation of halogenated hydrocarbons from effluent process streams is generally expensive. The relative expense of the removal is reduced, however, if the halogenated hydrocarbons from the separation are sufficiently pure as to be reusable. It is therefore desirable to provide a separation process for the removal of halogenated hydrocarbons which will result in relatively pure halogenated hydrocarbon product.

Halogenated hydrocarbons are often found in the solvent-laden air (SLA) of process effluent streams. Impurities such as alcohols, ketones and esters may also be present. A common method of removing the halogenated hydrocarbons and impurities from these SLA streams is to pass the SLA through one or more beds of activated carbon. The halogenated hydrocarbons and impurities will be adsorbed onto the carbon, resulting in a relatively pure air product leaving the bed. Periodically, the beds are regenerated with steam, after which the halogenated hydrocarbons, steam, and other impurities are condensed. Disposal of the condensation product is strictly regulated and expensive.

A solvent stream containing halogenated hydrocarbons, water, and alcohol, ketone or ester impurities is difficult to separate into the respective components as these compounds are not readily separable by distillation or other known separation processes. Some ketones and alcohols are slightly soluble in the halogenated hydrocarbons, and can form azeotropes with the halogenated hydrocarbons. It would accordingly be desirable to provide a process which would successfully separate halogenated hydrocarbons from water and these ketone and alcohol impurities to an extent that reuse of the halogenated hydrocarbons is possible.

SUMMARY OF THE INVENTION

It is an object of the invention to provide a process for the recovery of halogenated hydrocarbons from solvent streams.

It is another object of the invention to provide a process which recovers halogenated hydrocarbons at a purity sufficient to permit reuse of the halogenated hydrocarbons.

It is yet another object of the invention to provide a process for the recovery of halogenated hydrocarbons from solvent streams in which alcohols, ketones, esters and other impurities may be present.

It is still another object of the invention to provide a process for the recovery of halogenated hydrocarbons from solvent streams in which alcohols, ketones, esters and other impurities may be separately recovered.

These and other objects are accomplished by a process in which solvent streams containing halogenated hydrocarbons, water, and impurities such as ketones, alcohols and esters are treated by a first separation step, preferably decantation. The separation produces a halogenated hydrocarbon rich fraction containing some water and impurities, and a water rich fraction containing the impurities and some halogenated hydrocarbons.

The halogenated hydrocarbon rich fraction is passed to a first separation step, preferably a liquid-liquid extraction in which the halogenated hydrocarbons are contacted in counter-current flow with relatively pure water. The impurities, generally alcohols, ketones and esters, have a greater affinity for the water, and therefore impurity concentrations in the halogenated hydrocarbons leaving this extraction step are greatly reduced. Water and impurities separated by the liquid-liquid extraction step can be passed to the water rich fraction of the initial separation step for further treatment.

The halogenated hydrocarbons leaving the liquid-liquid extraction step may be relatively pure, although some water and impurities will generally be present. The halogenated hydrocarbon product can therefore be passed to a second separation step, preferably distillation, by which further removal of water and impurities from the halogenated hydrocarbons is accomplished by azeotropic distillation. The liquid-liquid extraction step will generally remove sufficient amounts of impurities such that azeotropic concentrations are sufficiently reduced so that purification of the halogenated hydrocarbons by distillation is possible. Water and impurities leave at an upper section of the distillation column, and are condensed in a suitable overhead condenser. A portion of the condensate can be returned to the column as reflux, while the remaining condensate is returned to the liquid-liquid extraction step.

Halogenated hydrocarbons preferably leave the distillation column as a vapor draw from a lower section of the column. The halogenated hydrocarbon product is condensed in one or more condensation steps, after which it can be stored or reused. Some very small quantities of water and impurities may remain in this product, which may not be suitable for certain product specifications. These specifications can usually be met by further processing the condensed halogenated hydrocarbon product in one or more additional separation steps, such as filtration through a molecular sieve or drying in a desiccant drier.

It is preferable to operate the halogenated hydrocarbon distillation step at elevated pressures, such that vapors leaving the distillation column can be condensed with water at ambient temperatures, rather than necessitating chilled water. Preferable pressures are between about 15 PSIG and about 50 PSIG. Pressure can be maintained by the introduction of nitrogen or other inert gas into the column, preferably in the distillate vapor condenser.

The water rich fraction leaving the decantation step is processed in at least one separation step intended to remove halogenated hydrocarbons. A suitable process is distillation. The halogenated hydrocarbons will leave at an upper section of the column with small amounts of water and impurities. These overhead vapors are preferably condensed in a suitable condensation step, and are returned to the decantation step.

Water having reduced amounts of halogenated hydrocarbon can be withdrawn from a lower section of the water distillation column. Significant amounts of impurities will remain in this water. The impurities are removed in at least one additional water rich fraction separation step, preferably a second distillation. The impurities, generally ketones, alcohols and esters having lower boiling points than water, will exit from a top section of the column, and substantially pure water will exit from the bottom of the column. This water will normally be sufficiently pure to sewer, however, it is preferable to use at least a portion of this product water in the halogenated hydrocarbon liquid-liquid extraction column.

The invention is useful to recover a variety of halogenated hydrocarbons including the fluorocarbons and the chlorinated hydrocarbons. The invention will also separately recover a number of alcohol impurities, including methanol, ethanol, isopropanol, and the like. Ketone impurities recoverable by the inventive process include acetone, methyl ethyl ketone, and methylisobutyl ketone. Ester impurities recoverable by the inventive process include ethylacetate, n-propylacetate and isopropylacetate.

BRIEF DESCRIPTION OF THE DRAWINGS

There are shown in the drawing embodiments which are presently preferred it being understood, however, that the invention is not limited to the precise arrangements and instrumentalities shown, wherein:

FIG. 1 is a schematic diagram of a process according to the invention.

DETAILED DESCRIPTION OF THE PREFERRED EMBODIMENTS

A preferred process for removing halogenated hydrocarbons from a solvent stream according to the invention is shown in the schematic of FIG. 1. The solvent stream can be a liquid stream, but normally will comprise a mixture of vapors exiting carbon adsorption beds during regeneration of the beds. The solvent stream contains regeneration steam, halogenated hydrocarbons, and generally some amount of alcohol, ketone or ester impurities. These vapors are condensed in a suitable condenser 10. Liquid product from the condenser 10 exits through a path 12 to an initial solvent stream separation step, preferably decantation in a suitable decanter 16. The decantation step separates the solvent stream into a halogenated hydrocarbon rich fraction containing some water and impurities, and a water rich fraction containing most of the impurities and some halogenated hydrocarbons.

The halogenated hydrocarbon rich fraction is withdrawn from the bottom portion of the decanter 16 and exits through a decanter halogenated hydrocarbon exit path 20, and can temporarily be stored in a halogenated hydrocarbon storage tank 22.

The halogenated hydrocarbon rich fraction leaves the halogenated hydrocarbon storage tank 22 through a halogenated hydrocarbon storage exit path 26. A suitable pump 28 can be provided for transport of the halogenated hydrocarbon from the halogenated hydrocarbon storage tank 22. The halogenated hydrocarbon rich fraction undergoes an initial separation adapted to reduce the concentration of the alcohol, ketone and ester impurities. A suitable separation process is liquid-liquid extraction. The halogenated hydrocarbon rich fraction is transferred by the pump 28 through an extraction halogenated hydrocarbon inlet path 32 to a suitable liquid-liquid extraction column 30. The halogenated hydrocarbon rich fraction preferably enters the extraction column 30 substantially at an upper portion of the column. Water enters the column through an extraction water inlet path 36, which is substantially at a bottom section of the column. The halogenated hydrocarbon rich fraction flows down the column and the water flows upward through the column.

The extraction column 30 can be of a suitable design, and will preferably have baffles, packing, or some other means for increasing the mass transfer surface. The water flows in counter-current contact with the halogenated hydrocarbon rich fraction. The alcohol, ketone and ester impurities have an affinity for the water, and are extracted out of the halogenated hydrocarbon fraction. The water and impurities exit at substantially a top portion of the column 30 through an extraction water exit path 38. A neutralizing/pH control agent may be added to the wash water entering the liquid-liquid extraction step for pH control of the final product, if necessary.

Halogenated hydrocarbons having a reduced impurity concentration exit from substantially a bottom portion of the extraction column 30 through an extraction halogenated hydrocarbon exit path 40. This halogenated hydrocarbon separation product will contain water and some remaining impurities. A second halogenated hydrocarbon separation step is therefore preferably provided to purify the halogenated hydrocarbons of water and these remaining impurities. This second separation process is preferably distillation, which can be accomplished in a suitable halogenated hydrocarbon distillation column 42. A suitable pump 44 can be used to transport the halogenated hydrocarbons through a halogenated hydrocarbons distillation inlet path 48. The halogenated hydrocarbons are preferably introduced substantially in a top section of the column. Heat is applied to the halogenated hydrocarbons distillation column 42 through a suitable reboiler 52. The bottoms of the halogenated hydrocarbon distillation column 42 exit through a halogenated hydrocarbon reboiler inlet path 54, and are returned by a halogenated hydrocarbon reboiler return path 55. A suitable heating fluid such as steam enters the reboiler 52 through a steam supply path 56 and exits through a condensate return path 60.

Water and remaining impurities containing some halogenated hydrocarbons exit a top portion of the distillation column 42 through an overhead exit path 62. The overhead product can be condensed in a suitable overhead condenser 64, which receives cooling water through a cooling water supply path 66 and returns cooling water through a cooling water return path 70. The condensed product leaves the overhead condenser 64 through an overhead condenser exit path 74. A portion of this condensate is returned to the distillation column 42 through a reflux path 76. Another portion of this condensate is returned to the inlet of the liquid-liquid extraction step through a water and impurities return path 80.

Halogenated hydrocarbons are removed from the halogenated hydrocarbon distillation column 42 as a vapor draw through a halogenated hydrocarbon vapor exit path 84 which is taken from a bottom section of the distillation column 42. The halogenated hydrocarbon vapor draw is condensed in a suitable halogenated hydrocarbon product condenser 86. The condenser 86 receives cooling water through a cooling water supply path 88, which water exits through a cooling water return path 90. Condensate leaves the condenser 86 through a halogenated hydrocarbon condensate exit path 94. A second halogenated hydrocarbon condenser 98 can be provided, if necessary. The second condenser 98 receives cooling water through a cooling water supply path 100, which water is returned through a cooling water return path 102. Condensate leaves the second condenser 98 through a condensate exit path 104, and can be passed to a halogenated hydrocarbon product receiver 108.

The halogenated hydrocarbon distillation column 42 is preferably operated at elevated pressures so as to permit the condensation of certain low temperature boiling halogenated hydrocarbons, the boiling temperatures of which are less than about 130 degrees F. The vapor draw is condensed by cooling water at substantially ambient temperatures. Lower purification column pressures require chilled water for this condensation, with a resulting increased operating expense. Preferable purification column pressures are between about 15 PSIG and about 50 PSIG. Pressure in the purification column may be adjusted by the introduction of suitable amounts of nitrogen or other noncondensable inert gases. These compounds can be introduced at suitable locations in the column, for example, at the overhead condenser 64. The column can be operated at about atmospheric pressure when processing high-temperature-boiling halogenated hydrocarbons, with boiling temperatures of about 130 degrees F. or greater.

The halogenated hydrocarbon product leaving the halogenated hydrocarbon distillation column 42 will be substantially pure, and may meet product specifications. Halogenated hydrocarbon product may then be withdrawn from the halogenated hydrocarbon product receiver 108 for reuse. Alternatively, strict product purity requirements may require some further treatment of the halogenated hydrocarbons. The halogenated hydrocarbons may exit the halogenated hydrocarbon product receiver 108 through a receiver exit path 110. A suitable pump 112 can be utilized to transport the halogenated hydrocarbons through a dryer inlet path 114 to one or more drying steps as indicated by the dryers 118. The drying steps may be selected from several suitable dehydration processes including filtration through molecular sieves or drying in desiccant dryers. Product leaving the dryers 118 is substantially pure halogenated hydrocarbon, and can exit the process through a halogenated hydrocarbon product exit path 122 to a suitable halogenated hydrocarbon storage facility 124.

The water rich fraction leaves the decanter 16 through a decanter water exit path 130. The water rich fraction may be retained temporarily in a suitable water storage tank 132. Water leaving the halogenated hydrocarbon liquid-liquid extraction column 30 through the extraction water exit path 38 can also be introduced to the water storage tank 132 for treatment with the water rich fraction leaving the decanter 16. The water rich fraction leaves the water storage tank 132 through a water storage tank exit path 136. A suitable pump 138 can be utilized to transport the water fraction to an initial separation process, preferably distillation. The pump 138 transports the water rich fraction through a water distillation inlet path 140 to substantially the top portion of a suitable water distillation column 144. The water distillation column 144 is heated by circulation through a reboiler path 146 which communicates with a water distillation water exit path 148 located substantially at a bottom portion of the water distillation column 144. A reboiler 150 of suitable design receives a suitable heating fluid such as steam through a steam supply 152, which exits the reboiler 150 through a condensate return path 154.

Halogenated hydrocarbons with some water and impurities exit the top of the water distillation column 144 through a water distillation overhead exit path 158. A suitable condenser 160 can be provided, as at the top of the water distillation column 144, to cool and condense the overhead vapors leaving the water distillation column 144. The condenser 160 receives cooling water through a cooling water supply path 162, which water exits the condenser 160 through a cooling water return path 164. The overhead product condensate can be returned to the decanter 16 through a water distillation overhead return path 168.

The purified product water from the water distillation column 144 is removed from substantially a bottom portion of the column 144 through the water distillation water exit path 148. Water leaving the water distillation column 144 will be substantially free of halogenated hydrocarbons, but will include significant amounts of ketone, alcohol and ester impurities. These impurities can be removed in a second separation step, preferably distillation. Water exiting the water distillation column 144 can be transported by a suitable pump 174 through a second water distillation water inlet path 176 to a second water distillation column 180. Water and impurities enter the second water distillation column 180 at substantially a top section of the column. Water exits a bottom section of the second water distillation column 180 through a second water distillation water exit path 181. Heat is supplied to the column through a reboiler path 182 which communicates between the second water distillation water exit path 181 and a suitable reboiler 184. The heated fluid is returned to the column 180 through a return path 185. The reboiler 184 receives heating fluid such as steam through a steam supply path 186, which exits the reboiler 184 through a condensate return 188.

Impurities leave the top of the second water distillation column 180 at an overhead impurity exit path 192. The impurities may be at the azeotropic concentration with water. The vapors can be condensed in a suitable condenser 196, which receives cooling water from a cooling water supply 198 and which returns water to a cooling water return path 202. The overhead product impurity condensate leaves the condenser 196 through a condenser impurity exit path 200. A portion of the overhead product condensate is returned to the impurity stripping column 180 through a reflux path 204. The remaining impurities are transferred through an impurity product exit path 208 to a suitable impurity product storage facility 212.

Water leaving the second water distillation column 180 can be sufficiently pure to be sewered as through a sewer path 218. It is preferred, however, to reuse this product water in the liquid-liquid extraction column 30. A suitable pump 222 can be utilized to transport the water to the extraction column 30. The water preferably is passed through a suitable cooler 226 prior to entry into the liquid-liquid extraction column 30. Water enters the cooler 226 through a cooling water supply path 228, and exits through a cooling water return path 230.

The invention is capable of recovering many different kinds of halogenated hydrocarbons, including the fluorocarbons and the chlorinated hydrocarbons. The invention is also capable of separately recovering many different ketone, alcohol and ester impurities. Examples of suitable alcohols include methanol, ethanol, isopropanol, and the like. Ketone impurities recoverable by the inventive process include acetone, methyl ethyl ketone, and methylisobutyl ketone. Ester impurities recoverable by the inventive process include ethylacetate, n-propylacetate and isopropylacetate.

In a particular embodiment, the invention is useful for recovering halogenated hydrocarbons from a solvent stream including isopropyl alcohol and water. This solvent stream is decanted to produce a halogenated hydrocarbon fraction and a water fraction including the isopropyl alcohol. The halogenated hydrocarbon fraction is treated by liquid-liquid extraction with water. Isopropyl alcohol present in the halogenated hydrocarbon fraction as an impurity is removed by the water, and can be passed to the water fraction of the decantation for further treatment. The halogenated hydrocarbon fraction from the liquid-liquid extraction is distilled in a distillation column maintained at about 15 PSIG to allow the use of cooling water at about 85 degrees F. to condense the overhead vapor. Water and alcohol, along with some halogenated hydrocarbons, leaving the top of the column is returned to the liquid-liquid extraction step. The purified halogenated hydrocarbon fraction is removed from a bottom section of the column as a vapor draw which is condensed to the halogenated hydrocarbon product. This product may be further dehydrated, if necessary.

The water fraction is distilled in a first distillation step to remove solubilized halogenated hydrocarbons, which exit at a top section of the column. These halogenated hydrocarbons are condensed and passed to the decantation step. The water fraction leaves the bottom section of the column and is passed to a second distillation step adapted to remove the isopropyl alcohol from the water. The isopropyl alcohol exits at a top section of the column at the azeotropic concentration (88 wt %). A portion of the isopropyl alcohol product is returned to the column as reflux and the remaining portion is withdrawn from the process. Water exits at a bottom section of the column with approximately 10-20 ppm of isopropyl alcohol. This product is suitable for sewering, or other use, although a portion is preferably cooled and recycled to the liquid-liquid extraction step.

The operating temperatures, pressures and concentrations will normally be variables determinable by known process engineering design methods for the particular job at hand. Particular selection, sizing and precise layout of the process equipment must, of course, depend upon the operation parameters and conditions. The number, type, dimension and design of the decanters, pumps, columns, tanks and condensers, for example, can vary. Accordingly, this invention may be embodied in other specific forms without departing from the spirit or essential attributes thereof, and reference should therefore be made to the following claims, rather than the foregoing specification, as indicating the scope thereof.

We claim:

1. A process for recovering halogenated hydrocarbons from solvent streams including water and at least one impurity, comprising the steps of:
   (a) separating the solvent stream into a halogenated hydrocarbon rich fraction containing water and impurity, and a water rich fraction containing impurity and halogenated hydrocarbon;
   (b) separating impurity from the halogenated hydrocarbon rich fraction of step (a), said separation including liquid-liquid extraction with water;
   (c) separating said impurity and halogenated hydrocarbon from said water fraction of step (a), said separation step including distillation and producing a product water;
   (d) recycling said product water from step (c) to the liquid-liquid extraction of step b) for contact with said halogenated hydrocarbon rich fraction.

2. The process of claim 1, wherein said separation step (a) is decantation.

3. The process of claim 2, wherein said liquid-liquid extraction step of said impurity separation step (b) is followed by a second halogenated hydrocarbon rich fraction separation step adapted to remove remaining water and impurity from said halogenated hydrocarbon rich fraction, and to product a halogenated hydrocarbon product.

4. The process of claim 3, wherein said second halogenated hydrocarbon rich fraction separation step comprises distillation.

5. The process of claim 4, wherein said second halogenated hydrocarbon rich fraction separation step is conducted at a pressure of between about 15 PSIG and about 50 PSIG.

6. The process of claim 5, wherein said elevated pressure is maintained by the introduction of nitrogen at said second halogenated hydrocarbon rich fraction separation step.

7. The process of claim 4, wherein said halogenated hydrocarbon product from said second halogenated hydrocarbon rich fraction separation step is further processed in a dehydration step.

8. The process of claim 2, wherein said water rich fraction separation step (c) comprises a first distillation step adapted to separate halogenated hydrocarbons from said water rich fraction and to produce a product water, followed by a second distillation step adapted to remove impurity from said water fraction.

9. The process of claim 1, wherein said halogenated hydrocarbons include at least one of chlorinated hydrocarbons and fluorocarbons.

10. The process of claim 1, wherein said impurity comprises at least one of the group consisting of ketones, alcohols and esters.

11. The process of claim 10, wherein said ketones include acetone, methyl ethyl ketone, and methylisobutyl ketone.

12. The process of claim 10, wherein said alcohols include methanol, ethanol, and isopropanol.

13. The process of claim 10, wherein said esters include ethylacetate, n-propylacetate and isopropylacetate.

14. A process for recovering halogenated hydrocarbons from solvent streams including said halogenated hydrocarbons, water, and at least one impurity selected from the group consisting of ketones, alcohols and esters, said process comprising the steps of:
   (a) separating said solvent stream into a halogenated hydrocarbon rich fraction containing water and impurity, and a water rich fraction containing said impurity and halogenated hydrocarbon;

(b) separating said impurity from said halogenated hydrocarbon rich fraction of step (a), said separation step including a liquid-liquid extraction step in which said halogenated hydrocarbon rich fraction is contacted with water;

(c) separating halogenated hydrocarbon from said water rich fraction of step (a) in a first water rich fraction distillation step, said first water rich fraction distillation step producing an intermediate water product and a halogenated hydrocarbon product, said halogenated hydrocarbon product being returned to said separation step (a);

(d) separating impurity from said intermediate water product of step (c) in a second water rich fraction distillation step, said second water fraction distillation step producing a water product and an impurity product; and, (e) returning at least a portion of the water product of step (d) to said liquid-liquid extraction of step (b).

15. The process of claim 14, wherein said separation step (a) is decantation.

16. The process of claim 15, wherein said liquid-liquid extraction step of said separation step (b) is adapted to reduce the concentration of said impurity in said halogenated hydrocarbon rich fraction, and produces an intermediate halogenated hydrocarbon product, said intermediate halogenated hydrocarbon product being distilled in a distillation step to produce a halogenated hydrocarbon product and a water product, said water product being returned to said liquid-liquid extraction step.

17. A process for recovering halogenated hydrocarbons from steam and solvent vapors produced during the regeneration of a carbon adsorption bed, said steam and solvent vapors including said halogenated hydrocarbons and at least one impurity selected from the group consisting of ketones, alcohols and esters, said process comprising the steps of:

(a) condensing said steam and solvent vapors;

(b) separating said condensate of step (a) into a halogenated hydrocarbon rich fraction containing water and impurity, and a water rich fraction containing impurity and halogenated hydrocarbon;

(c) separating said impurity from said halogenated hydrocarbon rich fraction in a liquid-liquid extraction step contacting said halogenated hydrocarbon rich fraction is contacted with water, and producing an impurity product and an intermediate halogenated hydrocarbon product;

(d) returning said impurity product of said liquid-liquid extraction of step (c) to said separation step (b);

(e) separating water from said intermediate halogenated hydrocarbon product, said separation comprising at least one distillation step;

(f) separating halogenated hydrocarbon from said water rich fraction in a first water rich fraction distillation step, said first water rich fraction distillation step producing a halogenated hydrocarbon separation product and an intermediate water product containing impurity;

(g) passing said halogenated hydrocarbon separation product of step (f) to said separation step (b);

(h) separating said impurity from said intermediate water product of step (f) in a second water rich fraction distillation step, said second water rich fraction distillation step producing an impurity product and a water product.

18. The process of claim 17, wherein said at least a portion of the water product of step (h) is returned to the liquid-liquid extraction of step (c).

* * * * *